United States Patent
Ichihara (10) Patent No.: US 8,191,453 B2
(45) Date of Patent: Jun. 5, 2012

(54) SPECIMEN SLICING GUIDE, SPECIMEN SLICING APPARATUS AND METHOD OF USING THE SAME

(76) Inventor: Shu Ichihara, Nagoya (JP)

( * ) Notice: Subject to any disclaimer, the term of this patent is extended or adjusted under 35 U.S.C. 154(b) by 482 days.

(21) Appl. No.: 12/472,275

(22) Filed: May 26, 2009

(65) Prior Publication Data

US 2009/0293689 A1 Dec. 3, 2009

(30) Foreign Application Priority Data

May 30, 2008 (JP) ................ P2008-143179

(51) Int. Cl.
*G01N 1/28* (2006.01)
(52) U.S. Cl. ........ 83/466.1; 83/522.19; 83/763; 83/827; 30/293; 30/358; 269/54.1; 269/87.2
(58) Field of Classification Search ............ 83/455, 83/456, 466.1, 468–468.2, 522.18, 522.19, 83/761–765, 821, 827; 30/289, 290, 293, 30/322, 323, 358, 359, 361; 269/54.1–54.5, 269/87.1, 87.2
See application file for complete search history.

(56) References Cited

U.S. PATENT DOCUMENTS

| | | | | | |
|---|---|---|---|---|---|
| 1,517,931 | A | * | 12/1924 | Wible | 30/358 |
| 1,626,922 | A | * | 5/1927 | Downs | 30/124 |
| 1,703,154 | A | * | 2/1929 | Lanzkron | 83/762 |
| 1,823,608 | A | * | 9/1931 | Kalkanis | 269/15 |
| D168,127 | S | * | 11/1952 | Schoenfeld | D7/683 |
| D169,827 | S | * | 6/1953 | Schoenfeld | D7/683 |
| 5,148,729 | A | | 9/1992 | Krumdieck | |
| 6,722,241 | B1 | * | 4/2004 | Anayas | 83/459 |
| 7,219,884 | B2 | * | 5/2007 | Morales | 269/53 |
| 2004/0175820 | A1 | | 9/2004 | Shigematsu et al. | |
| 2010/0050838 | A1 | | 3/2010 | Noguchi et al. | |

FOREIGN PATENT DOCUMENTS

| | | |
|---|---|---|
| DE | 493712 | 2/1930 |
| FR | 1.030.314 | 6/1953 |
| JP | 2006-038466 A | 2/2006 |
| JP | 4392457 B2 | 1/2010 |
| WO | 96/08208 A1 | 3/1996 |
| WO | 00/37918 A2 | 6/2000 |
| WO | 02/088668 A1 | 11/2002 |
| WO | 2004/030516 A2 | 4/2004 |
| WO | 2008/053916 A1 | 5/2008 |

OTHER PUBLICATIONS

Rosai J., Rosai and Ackerman's Surgical Pathology, 2004, pp. 25-37, Ninth Edition, Mosby, Edinburgh.
Extended European Search Report dated Feb. 22, 2011, including Search Report, Search Opinion and searched and examined claims.

* cited by examiner

*Primary Examiner* — Edward Landrum
(74) *Attorney, Agent, or Firm* — J-Tek Law PLLC; Jeffrey D. Tekanic (57) ABSTRACT

A specimen slicing guide for use in slicing a biopsy specimen taken from a human patient or an animal patient includes a base extending in a longitudinal direction. A plurality of needles extends substantially perpendicularly to the base and the needles are spaced along the longitudinal direction of the base. Two specimen slicing guides are coupled via at least one link, which is adapted to allow an adjustable spacing of the two specimen slicing guides in a parallel relationship. A method of cutting a biopsy specimen includes fixing the biopsy specimen relative to a support surface using the needles of two, parallel-arranged specimen slicing guides, inserting a cutting tool between corresponding needle gap pairs and then downwardly moving the cutting tool under guidance of adjacent needles.

20 Claims, 6 Drawing Sheets

SPECIMEN SLICING GUIDE, SPECIMEN SLICING APPARATUS AND METHOD OF USING THE SAME

CROSS-REFERENCE

This application claims priority to Japanese patent application no. P2008-143179, filed 30 May 2008, the contents of which are fully incorporated herein by reference.

1. Technical Field

The present invention relates to a specimen slicing guide, a specimen slicing apparatus and a method of using the same to slice a biopsy specimen taken from a human or an animal patient.

2. Background Art

Pathological examinations are conducted on organ or tissue specimens obtained from a human or animal patient, e.g., by performing a biopsy or a surgical operation, for research purposes and to diagnose diseases. A pathological examination generally includes, but is not limited to, the steps of cutting the biopsy specimen into slices or sections and then visually observing the slices (pathological specimens) using a microscope or other imaging apparatus. In more detail, the biopsy specimen may be processed, e.g., by first cutting it by hand with a knife into one or more slices, treating one or more of the slices with alcohol, xylene or other solvents, embedding the treated slice(s) in paraffin and then cutting the slice (s) again using a microtome into one or more thinner slices, usually transparently thin slices. The thinner slices may optionally be stained with a dye such as hematoxylin-eosin (H&E stain) prior to the visual observation step.

For example, when a pathological examination is performed for the purpose of detecting and/or diagnosing the stage of stomach cancer (neoplasm), all or a part of the stomach is surgically excised, the specimen is cut into one or more slices, the slice(s) is/are stained and the stained pathological specimen(s) is/are examined by the surgeon, a pathologist and/or another technician. Additional steps, e.g. such as but not limited to the steps noted above, may also be performed during the pathological examination.

This pathological examination procedure enables a determination of whether cancer (neoplasm) is present, what type of neoplasm is present (e.g., benign or malignant), how far the cancer has spread (including the condition of the margin of the specimen), the stage of the cancer, whether there is any vascular invasion, etc.

Herein, the phrase "the margin of the specimen" means the end of the biopsy specimen along the cut that was made to excise the tissue or organ from the patient. Information about the interior of the specimen is also important in order to accurately diagnose the condition of the margin. If the condition of the margin and the condition of the interior are both accurately diagnosed, the spread of stomach cancer or other disease under investigation can be diagnosed more precisely.

It is often desirable to prepare a plurality of uniformly thin slices from the biopsy specimen. In this regard, it may be desirable that each individual slice or segment has a uniform thickness across its entire cross section. In addition, it also may be desirable in certain investigations that all slices or sections have the same uniform thickness.

Conventionally, the pathologist, an assistant to the pathologist, a technician or another person skilled in preparing tissue samples (hereinafter, collectively, the "pathologist, etc.") would prepare the tissue samples by holding the biopsy specimen with one hand (such as the left hand) while slicing or cutting the biopsy specimen using a knife in the other hand (such as the right hand). Thus, in the past, the pathologist, etc. has been required to use only his or her eyesight and manual dexterity in order to prepare tissue slices having uniform thickness.

Consequently, such a conventional tissue sample preparation technique suffers from the problem that it is highly dependent on the skill of the pathologist, etc. and undesirable variations in tissue sample thickness often occur.

WO 00/37918 A2 discloses an apparatus for preparing tissue slices from a biopsy specimen. However, the slicing is performed mechanically and also involves simultaneously slicing a plurality of slices, whereby the slices inevitably end up being quite large.

SUMMARY

It is an object of the present invention to overcome one or more of the problems of the known art.

Techniques are disclosed herein for assisting the pathologist, etc. to prepare uniformly thin tissue slices from a biopsy specimen in a simple and reliable manner.

According to one aspect of the present teachings, a specimen slicing guide is disclosed for use in slicing a biopsy specimen taken from a human or animal patient. The specimen slicing guide comprises a plurality of needles extending from a base with gaps or spaces defined between adjacent needles. The needles preferably extend in parallel to each other and preferably all of the needles lie or extend in a common plane. The needles have distal ends or tips adapted to pierce a biopsy specimen. The arrangement of the base and needles may preferably have a substantially comb-shaped structure or tooth-shaped structure.

Preferably, the needles are spaced equidistantly along the longitudinal direction of the base and thus the gaps between adjacent needles have the same width. However, it is understood that other embodiments are also encompassed in which the gaps between adjacent needles are not equidistant. In this case, the specimen slicing guide can be advantageously employed in a method in which the narrower gaps are used for a knife or other cutting tool having a thinner blade, while wider gaps are used for a knife or other cutting tool having a thicker blade.

In other words, the spacing or width of the needle gaps is preferably set in accordance with the thickness of the blade(s) that will be used to cut the biopsy specimen, so that the adjacent needles provide a suitable guide when the pathologist, etc. moves the cutting tool downwardly through the biopsy specimen. In some applications of the present teachings, it may be desirable to utilize cutting tools with blades having different thicknesses when cutting the biopsy specimen.

In another aspect of the present teachings, a pair of specimen slicing guides is disposed in parallel to each other in a fixed relationship, e.g., preferably using one or more bridges or links configured to retain the pair of specimen slicing guides, thereby forming a specimen slicing apparatus. According to a preferred use of the specimen slicing apparatus, the biopsy specimen is placed on a support surface and the specimen slicing apparatus is then lowered from above the biopsy specimen toward the biopsy specimen, whereby the needles of each specimen slicing guide pierce the biopsy specimen, pass through the biopsy specimen, pierce and embed in the support surface and are thereby supported in and by the support surface.

In this way, the biopsy specimen can be easily fixed in a specified position relative to the support surface and the two specimen slicing guides are also themselves simultaneously fixed in the specified position.

In the alternative, it should be understood that the biopsy specimen can also be fixed in the specified position by first lowering one specimen slicing guide into one edge or end of the biopsy specimen and then subsequently lowering a second specimen slicing guide into an opposite end or edge of the biopsy specimen in a spaced relationship to the first specimen slicing guide. Thereafter, one or more bridges or links optionally may be utilized to fix the spaced relationship between the first and second specimen slicing guides prior to beginning the specimen cutting step. In the alternative, a support or retaining device may support the specimen slicing guide relative to the support surface without a direct connection between the two specimen slicing guides.

After the specimen slicing guides have been fixed in position relative to the biopsy specimen, the pathologist, etc. inserts a knife through a gap formed between two adjacent needles of a first specimen slicing guide and then through a corresponding, opposing gap formed between two adjacent needles of the second specimen slicing guide (hereinafter, "paired needle gaps"). Then, the knife is lowered along the paired needle gaps under guidance from the two sets of needles forming the paired needle gaps, thereby cutting the biopsy specimen.

The width of the "paired needle gaps" is the width of the gaps of the two adjacent needles in the two specimen slicing guides. If the gaps between these needles are relatively narrow in width, the paired needle gaps form a substantially two-dimensional (planar) space for guiding the knife or other cutting tool.

The biopsy specimen can be uniformly sliced into a plurality of tissue slices or tissue sections by repeating the above-mentioned cutting procedure using other paired needle gaps. Consequently, the present specimen slicing guides and methods of using the same enable the preparation of tissue slices having a uniform thickness over the entire cross section.

As was indicated above, the needles are preferably spaced apart equidistantly, such that all the gaps between adjacent needles have the same width. Such a specimen slicing guide can be utilized to prepare a plurality of tissue slices having the same thickness.

In another aspect of the present teachings, the needle gap between adjacent needles preferably substantially corresponds to the thickness of the knife blade or cutting tool that will be used to slice the biopsy specimen. In this case, when the pathologist, etc. inserts the blade into the paired needle gaps and the knife or cutting tool is lowered along the paired needle gaps, the knife is reliably and steadily guided by the two sets of needles that form the paired needle gaps. Accordingly, the biopsy specimen can be uniformly sliced in a more reliable manner. That is, it is possible for each tissue slice to be uniformly thick across its entire cross section, and also, it is possible for the plurality of tissue slices to each have the same thickness.

In this aspect as well, it is not necessary for the plurality of needles to be spaced equidistantly apart. Therefore, the present teachings also encompass an embodiment in which there are wider and narrower gaps among the plurality of gaps between adjacent needles. As was noted above, in this case, a knife having a thinner blade can be used in the narrower gaps and a knife having a thicker blade can be used in the wider gaps.

In another aspect of the present teachings, the base of the specimen slicing guide is preferably provided with one or more gap identification markers. For example, one or more of the gaps between adjacent needles is/are preferably marked with a gap identification marker on the base. The gap identification markers may be generic (i.e., not unique, e.g. dots or the same symbol) or may specifically identify the respective marked needle gaps using a set of different unique markers. In this aspect, the gap identification markers can be used as a visual reference for assisting the pathologist, etc. to readily identify corresponding paired needle gaps of two parallel-disposed specimen slicing guides. By using the convenient visual references, the pathologist, etc. can more quickly and reliably insert the knife into the appropriate paired needle gaps for cutting the biopsy specimen into the plurality of tissue slices.

In addition or in the alternative, the base may include one or more needle identification markers that is/are provided adjacent to or near one or more of the plurality of needles. Each needle identification marker may specifically and uniquely identify the marked needle. In this aspect as well, the needle identification markers can be used as a visual reference, so that the pathologist, etc. can more easily locate the corresponding set of paired needle gaps of the two parallel-disposed specimen slicing guides in order to perform the tissue slicing procedure more quickly and reliably.

In addition or in the alternative, one or more needle identification markers can be disposed directly on the needle(s) in order to specifically identify one or more of the needles. This would also assist in achieving the beneficial cutting effects noted above.

It is noted that the gap identification markers and/or needle identification markers may be, for example and without limitation, a set of symbols, such as alphabet letters or other characters, numerals, shapes, etc., and/or a set of different colors. Any visual indicator that will help the pathologist, etc. to more readily identify a corresponding set of paired needle gaps for inserting the cutting device is understood as falling within the scope of the present teachings.

In another aspect of the present teachings, a specimen slicing apparatus comprises a first specimen slicing guide, a second specimen slicing guide and at least one bridge or link coupling the first specimen slicing guide to the second specimen slicing guide. The bridge(s) or link(s) preferably is (are) configured to retain the first and second specimen slicing guides in a fixed, parallel relationship during a tissue slicing procedure. In this aspect, the pair of specimen slicing guides can be reliably positioned in an opposing state and the pathologist, etc. can easily lower the entire specimen slicing apparatus onto and through the biopsy specimen. Accordingly, the preparation of the biopsy specimen for slicing can be performed more easily.

The bridge(s) or link(s) may be designed to permanently maintain the first and second specimen slicing guides in a predetermined spaced relationship. On the other hand, it is more preferable that the specimen slicing guides and the bridge(s) or link(s) are designed to allow the pathologist, etc. to adjust the spaced relationship (i.e. the distance) between the specimen slicing guides. In the embodiment in which the spacing between the two specimen slicing guides is adjustable, biopsy specimens of various sizes can be accommodated by suitably adjusting the spacing between the two specimen slicing guides in accordance with the size of the biopsy specimen to be sliced.

In another aspect of the present teachings, a specimen slicing kit comprises either two specimen slicing guides or a specimen slicing apparatus according to the above teachings and a support surface for supporting the biopsy specimen. Preferably, the support surface comprises a resiliently elastic material, e.g., cork, and allows the needles to pierce the support surface and then reliably support the needles embedded in the support surface during the specimen cutting procedure.

In another aspect of the present teachings, the needles of the specimen slicing guide do not all lie or extend in a common plane. Instead, the needles may be offset from a longitudinal line extending along the base, wherein some needles are disposed on one side of the longitudinal line and some needles are disposed on the other side of the longitudinal line. For example, the needles may be disposed, e.g., in a jagged, zigzag or sinusoidal pattern as viewed along the longitudinal axis of the base.

If a second specimen slicing guide is configured in the same manner, the offset needles may serve as another visual aid to assist the pathologist, etc. in quickly and reliably identifying corresponding paired needle gaps in the two specimen slicing guides, thereby facilitating the tissue cutting procedure. In addition or in the alternative, by offsetting the needles in the cutting direction (i.e. a direction perpendicular to the longitudinal direction of the base), the specimen slicing guides can be supported in the support surface more stably during the tissue slicing procedure, optionally without the need for a link or bridge directly connecting the two specimen slicing guides. That is, if the needles are offset in the cutting direction, the specimen slicing guide may be able to better withstand forces applied in the cutting direction to prevent the specimen slicing guide from tipping over during the tissue slicing procedure.

Herein, the term "biopsy specimen" is not limited to the removal of internal organs and the like from a human or animal patient, but also encompasses excising tissue from a patient that forms a part of the outer surface of the patient, such as e.g., skin tissue.

Further objects, aspects, advantages and uses of the present teachings will become apparent after reviewing the following detailed description of embodiments of the present invention in conjunction with the appended drawings.

DETAILED DESCRIPTION OF THE PREFERRED EMBODIMENTS

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved specimen slicing guides, specimen slicing apparatus and specimen slicing kits, as well as methods of using the same.

Moreover, combinations of features and steps disclosed in the following detail description may not be necessary to practice the invention in the broadest sense, and are instead taught merely to particularly describe representative examples of the invention. Further, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Figure 1:
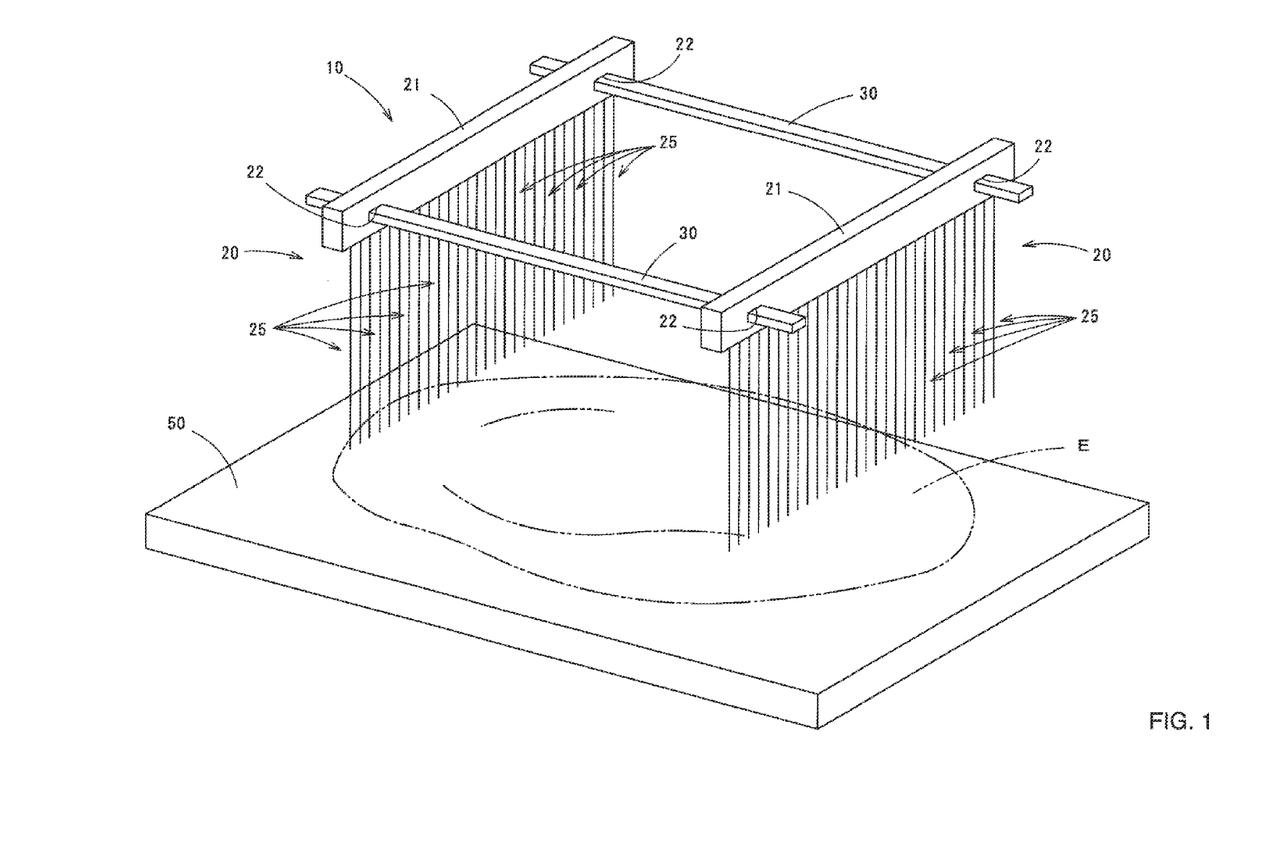
FIG. 1 shows an oblique view of a representative specimen slicing apparatus disposed above a biopsy specimen and a support surface.

FIG. 1 shows a first representative, non-limiting specimen slicing apparatus 10 and a support surface 50, which together provide a specimen slicing kit. The specimen slicing apparatus 10 includes a pair of specimen slicing guides 20 and a pair of links or bridges 30. This specimen slicing kit is preferably used with a cutting tool, such as a knife K (see FIGS. 4A and 4B).

Figure 2:
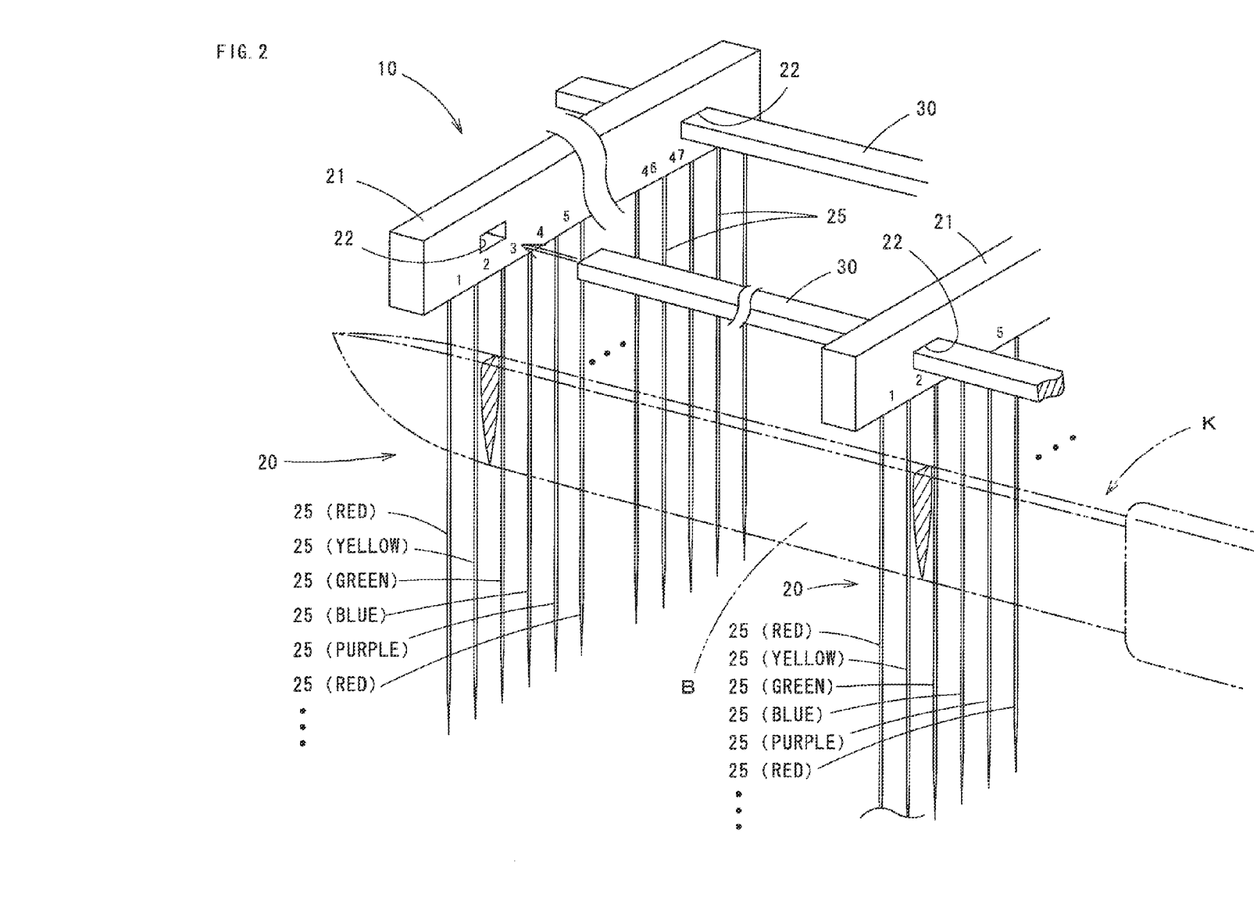
FIG. 2 shows a detailed oblique view of the representative specimen slicing apparatus of FIG. 1 with a knife blade inserted through one set of paired needle gaps, in which needle gap identification numbers are provided above each needle gap.

As shown in FIGS. 1 and 2, each of the specimen slicing guides 20 includes a base 21 and a plurality of needles 25, preferably 20 to 100 needles. The base 21 is preferably in the form of a bar or a strut that extends linearly. During the preferred use (see below), a longitudinal axis of the base 21 preferably extends substantially horizontally.

Each of the needles 25 preferably extends perpendicularly to the longitudinal axis of the base 21. During the preferred use (see below), the needles 25 preferably extend substantially vertically downward from the base 21.

All of the needles 25 preferably have the same shape and size. The needles 25 may each preferably have a circular cross section along their entire length. However, other cross-sectional shapes, such as e.g., a square cross section, are also useful in certain applications of the present teachings. The cross sectional shape of the needles 25 is not particularly limited.

The needles 25 are preferably arranged in a single straight row, uniformly spaced apart, in the longitudinal or lengthwise direction of the base 21. However, it is also possible to provide two or more rows of needles 25. Furthermore, the width or spacing between needles 25 may vary and the needles 25 are not required to extend in a straight line.

As shown in FIG. 2, the width of the gap between the needles 25 preferably substantially corresponds to the thickness of the blade B of the knife K. More preferably, the width substantially corresponds to the thickness of the largest width of the blade B of the knife K. That is, the gap between adjacent needles 25 is substantially the same as the thickness of the thickest portion of the blade B, but may be slightly wider than the blade thickness. For instance, the gap between adjacent needles 25 is preferably about 2 to 4 mm, although other widths may be useful depending upon the particular application of the present teachings.

In an alternate embodiment, the needles 25 may be spaced so as to be the same width or even slightly less than the width of the largest width of the blade B. In this case, it is preferably that the needles are resiliently elastic/bendable, so that the adjacent needles bend or deflect slightly outward when a blade B is inserted through the needle gap. In this case, the needles 25 would elastically urge the blade 25 from each side, thereby further guiding the blade B along a straight downward path. Optionally, the needles may be coated with a friction-reducing material, e.g. polytetrafluoroethylene and/or a lubricant, to reduce friction caused by the blade B closely contacting the needles 25 during the downward movement in this embodiment.

In the embodiment shown in FIG. 2, each of the bases 21 is provided with numerical identification markers corresponding to the gaps between the needles 25 (i.e. the gaps between adjacent needles 25) as well as colored identification markers for each needle 25. Herein, an identification marker for specifying a particular gap between the needles 25 will be called a "gap identification marker", while an identification marker for specifying a particular needle 25 will be called a "needle identification marker".

In this embodiment, the gaps between the needles 25 are numerically marked in a sequential manner, i.e. 1, 2, 3 . . . . Naturally, the present teachings are not limited in this regard. For example, the gap identification markers may be provided for only some of the gaps, such as e.g., only for even-numbered gaps or for gaps in multiples of five, ten, etc. Moreover, any kind of symbols, characters, graphics, colors or the like may be used instead of numbers or letters. Similarly, the needle identification markers are not limited to different colors and also may be any kind of symbols or graphics.

Figure 5:
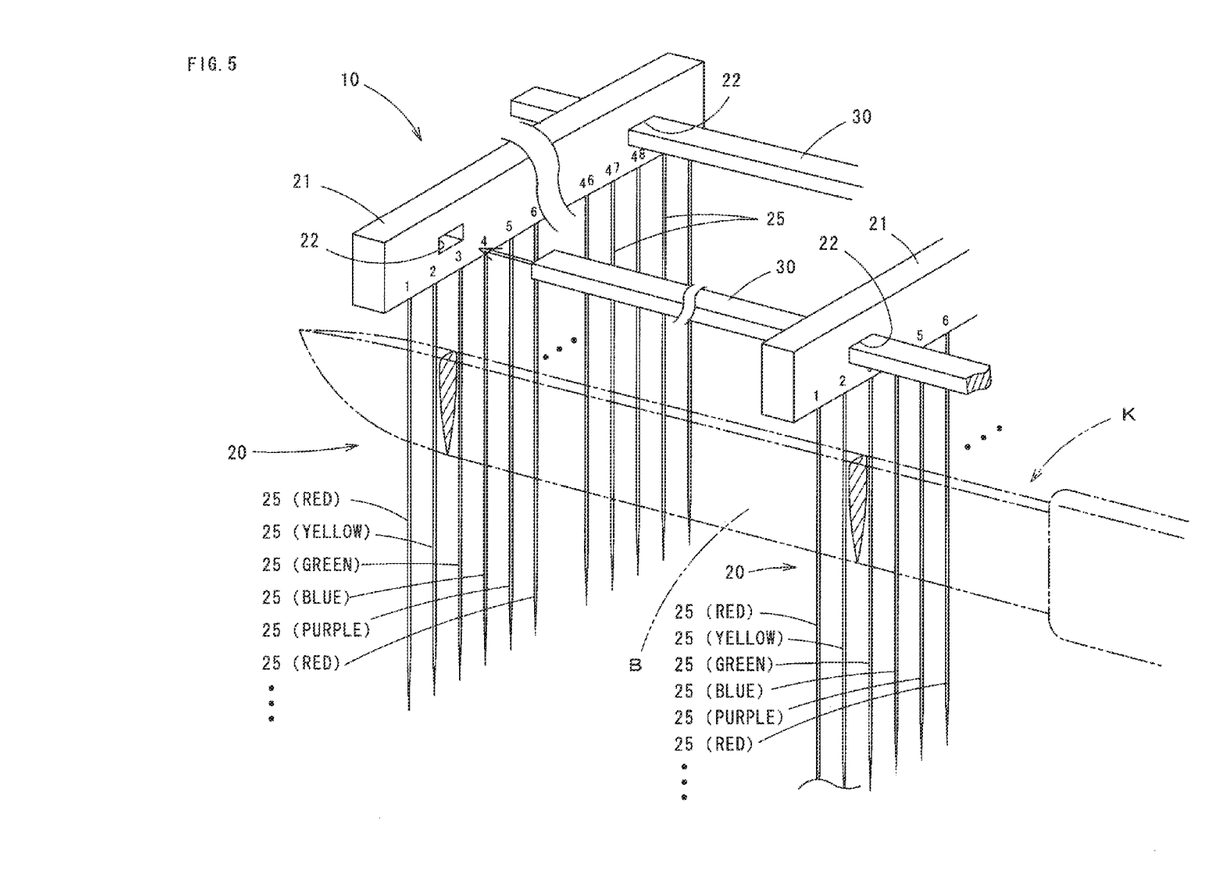
FIG. 5 shows an alternate embodiment, in which needle identification numbers are provided above each needle.

Although the needle identification markers are provided on the needles 25 in FIG. 2, the needle identification markers also be may be provided on the base 21 as shown in FIG. 5, instead of or in addition to the above-mentioned gap identification markers. In this regard, the needles 25 may be assigned sequential numerals (natural numbers), wherein e.g., the number "1" is associated with the first needle 25, the number "2" is associated with the second needle 25, and so forth. Again, it is not necessary to number all needles, as only a subset can be numbered in certain embodiments of the present teachings, e.g., even-numbered needles or needles in multiples of an integer, such as five or ten.

As shown in the representative embodiment of FIG. 2, different colors may be assigned to the needles 25 as "on-the-needle" identification markers. The color may be disposed along the entire length of the needles 25 or along only a portion of the length, e.g., only the top portion. In this representative embodiment, the first needle 25 is colored red, the second needle 25 is colored yellow, the third needle 25 is colored green, the fourth needle 25 is colored blue, and the fifth needle 25 is colored purple. The same pattern of coloration may be repeated for the subsequent needles 25 along the base 21. Again, such on-the-needle identification markers may be provided for less than all of the needles 25, such as only for even-numbered needles, or only for needles of certain integer multiples.

As shown in the Figures, two specimen slicing guides 20 are connected and supported at their bases 21 by the pair of links or bridges 30. The two guides 20 and the two links 30 collectively form a specimen slicing apparatus 10.

As a non-limiting embodiment of a connection or link between two specimen slicing guides 20, a pair of insertion holes or apertures 22 may be formed in each base 21 of the two specimen slicing guides 20. The links 30 extend through the insertion holes 22 of both specimen slicing guides 20 (bases 21) and are generally linear or straight in shape. Preferably, the holes 22 and links 30 have a uniform cross section (shape and size) along their entire length.

Preferably, the shape of the insertion holes 22 corresponds or substantially corresponds to the outer cross-sectional shape of the links 30. Thus, in the present example, the holes 22 are rectangular in order to match the rectangular shape of the links 30, whereby the links 30 and holes 22 have a rectangular cross section. However, other cross sections may be used with the present teachings, such as circular, semi-circular, triangular, square, hexagonal, etc.

Figure 3:
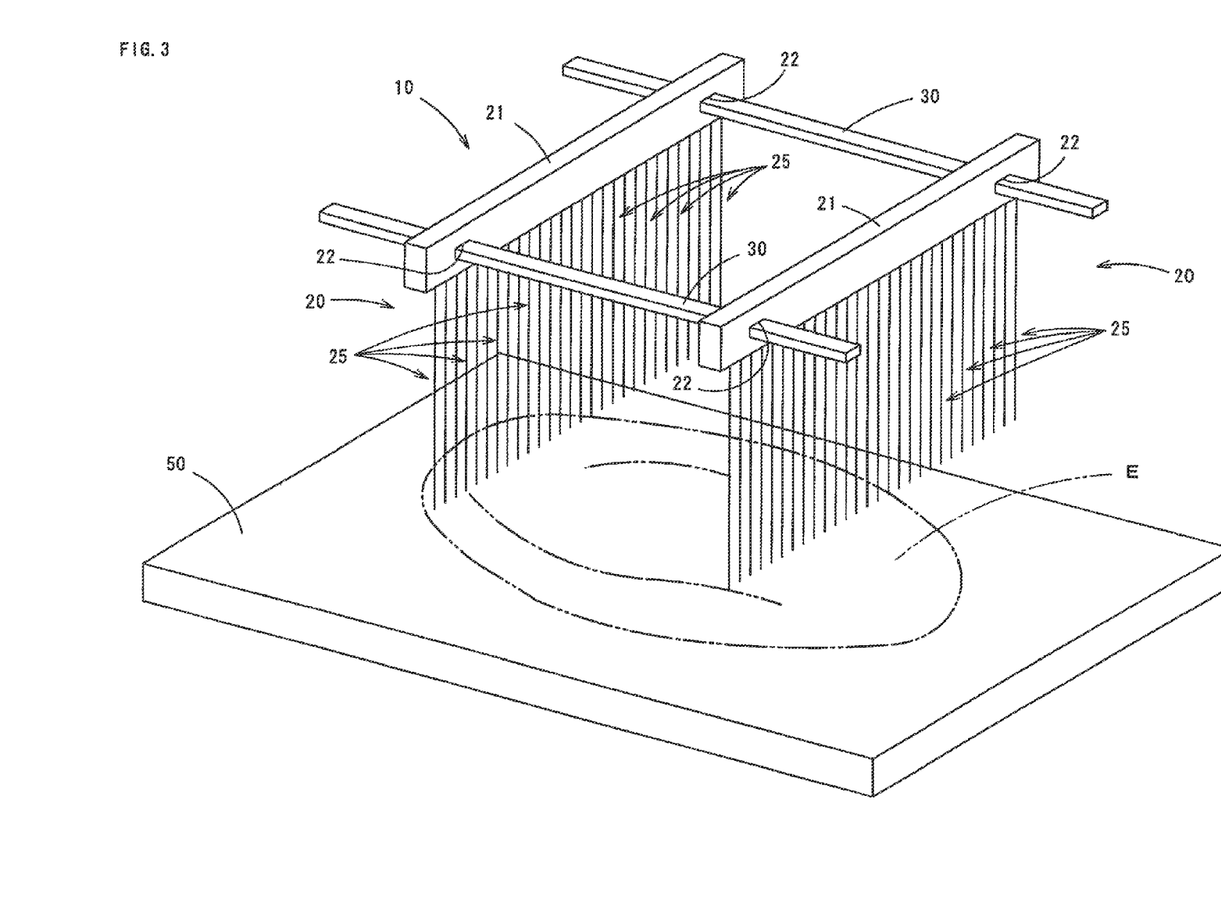
FIG. 3 shows an oblique view of the representative specimen slicing apparatus of FIG. 1, wherein the spacing between the two specimen slicing guides has been shortened.

It is preferable that the links 30 and bases 21 are configured so that the guides 20 are slidable relative to each other along the length of the links 30. This slidability enables the spacing between the two guides 20 to be changed in order to adapt the apparatus 10 to differently-sized biopsy specimens E. For example, FIG. 1 shows a state of the apparatus 10 in which the spacing between the two specimen slicing guides 20 has been lengthened, while FIG. 3 shows a state of the apparatus 10 in which the spacing between the two specimen slicing guides 20 has been shortened.

Preferably, retainers (larger than the insertion holes 22) are provided for temporarily affixing the links 30 relative to the bases 21, so that the bases 21 do not move, tip or slide relative to each other during a tissue slicing procedure. In addition or in the alternate, the retainer(s) may function to prevent the link(s) 30 from coming out of the insertion holes (22) when the pathologist, etc. adjusts the spacing or distance between two specimen slicing guides 20. As a non-limiting example, a first retainer may be fixedly attached at one end of each link 30 and a second retainer may be removably attached to the other end of the links 30.

In the alternative, one end of one of the links 30 may be fixedly attached to the same end of the other link 30 via a first connector that extends perpendicularly to the two links 30. Such a connector may be advantageously utilized to prevent the ends of the links 30 from coming loose, and also to maintain the links 30 in a specific positional relationship relative to each. The other end of the links 30 may be removably attached using a second connector extending perpendicularly to the two links 30.

Preferably, a gauge may be provided on one or both the links 30. The gauge may be advantageous to enable the pathologist, etc. to visually measure the distance between the two specimen slicing guides 20 (bases 21), and also to enable the spacing to be easily adjusted as desired.

The number of links 30 is not limited to two (a pair), and may be three or more. Furthermore, a single link 30 may be utilized, e.g., in the form of a single wide strip (one piece).

The support surface 50 (FIG. 1) preferably comprises cork or a cork-like material. The entire support structure may be formed from cork or in the alternative, a flat piece of cork may be laminated or otherwise attached to a foundation formed from another material. The advantage of using cork for the support surface 50 is that, when the distal ends of the needles 25 pierce the support surface 50 and become embedded in the support surface 50, the needles 25 are steadily supported in this pierced state. Thus, the specimen slicing guides 20 remain firmly affixed to the support surface 50 during the tissue slicing procedure and resist tipping over when a blade B passes through a particular needle gap, even if forces are applied to the specimen slicing guides 20 in the cutting direction.

The support surface 50 is not, however, limited to cork or cork-like materials. Any material can be used that can be pierced or penetrated by the distal ends of the needles 25 and then support the needles 25 during the tissue slicing procedure. In this regard, synthetic materials (e.g., foamed or rubber synthetic materials) or even certain soft woods may also be utilized and the present teachings are not limited in this regard, as long as the needles 25 can be reliably supported in the support surface 50.

A representative method for using the specimen slicing kit and its advantages and effects will now be described.

Figure 4A:
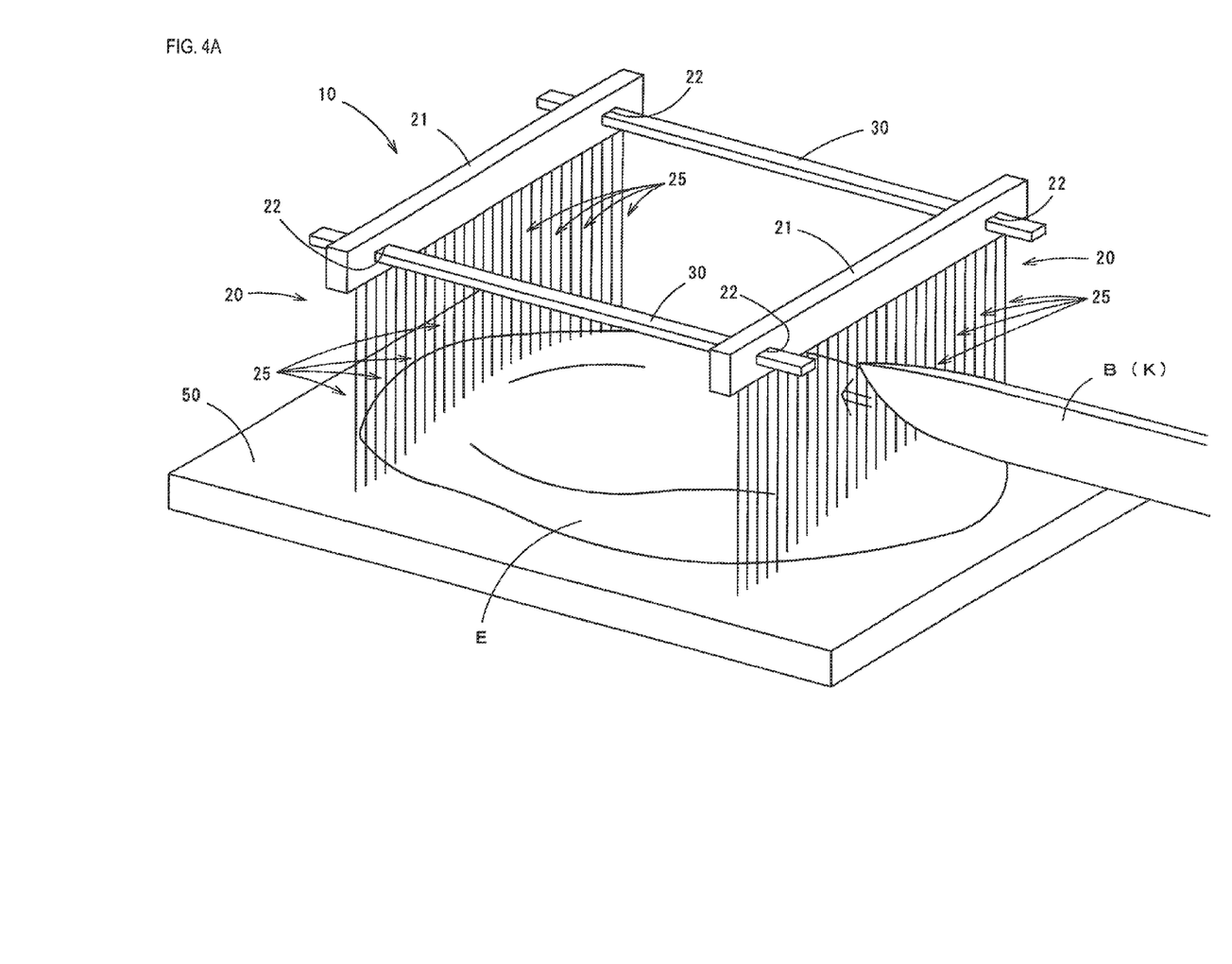
FIG. 4A shows an oblique view of the representative specimen slicing apparatus of FIG. 1, wherein a biopsy specimen is fixed in position relative to a support surface and a knife is ready to be inserted through corresponding paired needle gaps.

As shown in FIG. 4A, the pathologist, etc. first places a biopsy specimen E on the support surface 50. Either before or after the specimen placement step, the spacing between the two specimen slicing guides 20 in the specimen slicing apparatus 10 is adjusted in accordance with the size of the biopsy specimen E. For example, if the biopsy specimen E is relatively large, the spacing between the two specimen slicing guides 20 is increased (see FIG. 1), and if the biopsy specimen E is relatively small, the spacing between the two specimen slicing guides 20 is decreased (see FIG. 3). The determination of the most appropriate spacing may also depend upon the nature of the biopsy specimen E that will be sliced and is well within the skill of a pathologist, etc. in this field.

Next, as shown in FIG. 4A, the pathologist, etc. sticks the needles 25 of each of the specimen slicing guides 20 completely through the biopsy specimen E and embeds the distal ends of the needles 25 in the support surface 50. As a result, the needles 25 (i.e. the distal ends thereof) are maintained in the pierced/embedded state extending upwardly from the support surface 50. Moreover, the position of the biopsy specimen E is securely fixed relative to the support surface 50 and the specimen slicing guides 20 are themselves securely affixed in the support surface 50. The specimen slicing apparatus 10 is now positioned for slicing the biopsy specimen E.

Generally speaking, the biopsy specimen E is sliced or sectioned as follows. First, a knife K or other kind of cutting tool is inserted through corresponding needle gaps in the two specimen slicing guides 20 and then downwardly moved through the biopsy specimen E, whereby the needle gaps of the two specimen slicing guides 20 serve to reliably guide the downward movement of the knife K or other cutting tool and to ensure the production of tissue slices having a uniform thickness across the entire cross section of the tissue slice.

Figure 4B:
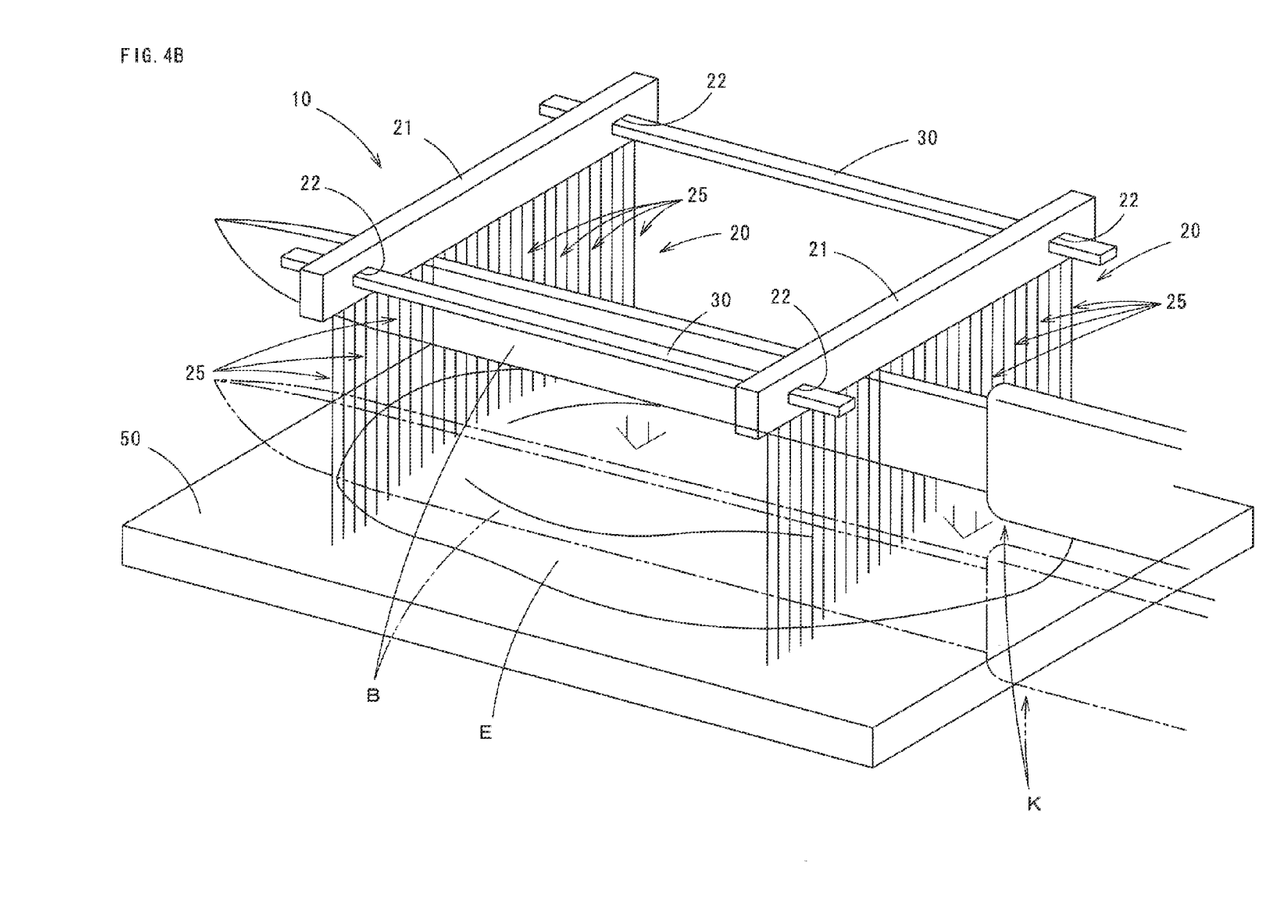
FIG. 4B shows an oblique view of the representative specimen slicing apparatus of FIG. 4A with the knife inserted through a pair of corresponding needle gaps and lowered (two-dot chain line) to make a slice of the biopsy specimen.

More specifically, as shown in FIGS. 4A and 4B, the pathologist, etc. inserts the knife K (i.e. the blade B) through a gap between the needles 25 of one of the specimen slicing guides 20, then all the way to the gap between the needles 25 of the corresponding other specimen slicing guide 20, as indicated by the blade B shown in solid lines in FIG. 4B. Then, the pathologist, etc. lowers the knife K in this inserted state to cut the biopsy specimen E, as indicated by the two-dot chain line in FIG. 4B.

Preferably, the pathologist, etc. begins the cutting procedure using a gap on one lateral side of the apparatus 10 and sequentially cuts the biopsy specimen E by laterally moving the knife K to the adjacent gaps until the necessary number of tissue slices has been prepared.

More specifically, the pathologist, etc. first inserts the blade B of the knife K into the space formed by the first gap of one of the specimen slicing guides 20 (a gap between adjacent needles 25) and the first gap of the other specimen slicing guide 20 (the first paired gap spaces). In a preferred embodiment, the pathologist, etc. may use the number "1" gap identification marker (see FIG. 2) on the base 21 of one of the specimen slicing guides 20 as a visual reference and the corresponding number "1" gap identification marker on the base 21 of the other specimen slicing guide 20 as a visual reference.

In addition or in the alternative, the pathologist, etc. may use the differently colored needles as visual references. For example, the pathologist, etc. can insert the blade B between the adjacent red and yellow needle identification markers for the first and second needles 25 of one of the specimen slicing guides 20 and then use the corresponding red and yellow needle identification markers to identify the corresponding first and second needles 25 of the opposing specimen slicing guide 20.

Thus, the pathologist, etc. can readily identify the appropriate paired needle gaps using the gap identification markers and/or the needle self-identification markers as convenient visual references.

As was indicated above, the cutting step is completed by lowering the knife K under the guidance of the two sets of corresponding needle pairs to cut the biopsy specimen E (FIG. 4B). Further tissue slices can be prepared by inserting the blade B into the space formed by the next adjacent gap of one of the specimen slicing guides 20 and the corresponding gap of the other specimen slicing guide 20 (the second paired gap spaces) and lowering the knife K in this inserted state (guided state) to cut the biopsy specimen E. This method is repeated as required in order to obtain the desired number of tissue slices.

Naturally, if thicker tissue slices are desired, it is not necessary to use every paired needle gap and instead, every other paired needle gap may be used or a larger multiple of gaps may be used.

When the biopsy specimen E has been sliced as above (that is, in the state immediately after the slicing), slicing cuts extend through the biopsy specimen E, but the biopsy specimen E maintains in the same overall shape it had prior to being sliced, because it is affixed at each end by the needles 25 of the two specimen slicing guides 20. Accordingly, in the state immediately after the slicing, the pathologist, etc. can easily assign position information (information about where each slice was located in the state prior to the slicing of the biopsy specimen E) to each slice, such as assigning a number to each slice. Once the position information has been assigned to the slices, the specimen slicing guides 20 may be removed and the tissue slices may then be separated from one another. One or more of the tissue slices may then be subjected to subsequent processing/treatment and analysis. This analysis information is combined with the position information for the slices, which enables a clear visualization of the distribution of a lesion in the biopsy specimen E as a whole, while also providing a pathological diagnosis.

As mentioned above, with the specimen slicing kit of the present teachings, the biopsy specimen E can be easily and reliably fixed in position relative to the support surface 50 by the plurality of needles 25 of the two specimen slicing guides 20. Further, the specimen slicing guides 20 themselves can be easily and reliably fixed to the support surface 50 using the plurality of needles 25.

In the state in which the biopsy specimen E and the specimen slicing guides 20 are fixed to the support surface 50, the blade B of the knife K is inserted into a particular paired needle gap and the knife K is lowered while being guided by the two pairs of needles 25, thereby ensuring that the biopsy specimen E is cut substantially vertically (in the direction of the two pairs of needles 25) and with the resulting tissue slices having a uniform thickness.

Thus, the biopsy specimen E can be sliced uniformly using the present specimen slicing kit and each slice preferably has the same thickness at all locations and all slices have the same thickness.

Furthermore, the present specimen slicing apparatus 10 may preferably provide advantageous visual guides, such as gap identification markers on the bases 21 of the specimen slicing guides 20 and/or needle identification markers on needles 25 and/or bases 21 of the specimen slicing guides 20.

The present teachings may be modified in various ways. For example, both the gap identification markers (such as numbers identifying the gaps between needles) and needle identification markers (such as colors identifying the needles) do not necessarily have to provided, and just one of them may be provided. In addition or in the alternative, the cross sectional shape of the needles 25 is not limited to being circular over the entire length of the needles and may have another shape (e.g., square or semi-circular) over part or all of the length. Also, the upper portion of the needles 25 may have a substantially linear cross sectional shape (e.g., in the form of a flat strip) extending in the lengthwise direction of the links 30.

The pair of specimen slicing guides 20 may be utilized to cut a biopsy specimen E without the pair of links 30. In this case, the pathologist, etc. may individually place two specimen slicing guides 20 on the support surface 50 in an opposing, parallel relationship. The specimen slicing guides 20 may then be utilized only supported by the needles 25 penetrating into the support surface 50 (i.e. without one or more links 30). In the alternative, one or more retaining elements may connect or couple the base 21 of each specimen slicing guide 20 directly to the support surface 50 (i.e. without a direct connection between the two specimen slicing guides 20) to provide additional support.

Furthermore, the link(s) 30 are not limited to rod-like projections that extend through the insertion holes 22 defined in the respective bases 21. Instead, the link(s) 30 may comprise a bridge element having one or more clamps that can be detachably affixed to the base(s) 21. The clamp(s) may be slidable or movable along the length of the bridge element in order to provide adjustable spacing between two specimen slicing guides 20. The skilled person will recognize that the link(s) 30 can be embodied in various forms that provide the function of enabling the spacing or distance between two specimen slicing guides 20 to be changed by the pathologist, etc. and the present teachings are not limited with respect to the form of the adjustable link(s) 30.

The techniques described above are preferably used to perform the first or initial cutting of a biopsy specimen into one or more tissue slices. Thereafter, the tissue slices prepared by cutting with the knife using the present specimen slicing guides may be further processed as discussed above in the introduction, e.g., by treating the tissue slices with alcohol, xylene or other solvents, embedding the treated tissue slices in paraffin and then cutting the embedded tissue slices into much thinner slices using a microtome.

The invention claimed is:

1. A specimen slicing apparatus for use in slicing a biopsy specimen taken from a human or an animal patient, the apparatus comprising:
    a first specimen slicing guide having a base extending in a longitudinal direction and a plurality of needles extending substantially perpendicularly from the base and being spaced along the longitudinal direction of the base, wherein distal ends of the needles are configured to pierce the biopsy specimen,
    a second specimen slicing guide having a base extending in a longitudinal direction and a plurality of needles extending substantially perpendicularly from the base and being spaced along the longitudinal direction of the base, wherein distal ends of the needles are configured to pierce the biopsy specimen and
    at least one link coupling the first and second specimen slicing guides in a spaced, parallel arrangement,
    wherein the first and second specimen slicing guides and the at least one link are configured to permit the spacing between the first and second specimen slicing guides to be adjusted while maintaining the needles of the first and second specimen slicing guides in a parallel relationship, and
    the needles are resiliently bendable.

2. The specimen slicing apparatus according to claim 1, wherein the needles are spaced equidistantly along the longitudinal direction of the base.

3. The specimen slicing apparatus according to claim 2, further comprising at least one visual reference selected from the group consisting of:
    a plurality of gap identification markers provided on the base,
    a plurality of needle identification markers provided on the base, and
    needle identification markers provided on two or more needles.

4. The specimen slicing apparatus according to claim 3, wherein the needles of each specimen slicing guide extend in a straight row.

5. The specimen slicing apparatus according to claim 4, wherein the at least one link is at least substantially linear.

6. The specimen slicing apparatus according to claim 5, wherein the at least one link extends through an insertion hole formed in the base of each specimen slicing guide, such that the specimen slicing guides are slidable relative to each other along the at least one link.

7. The specimen slicing apparatus according to claim 1, further comprising at least one visual reference selected from the group consisting of:
    a plurality of gap identification markers provided on the base,
    a plurality of needle identification markers provided on the base, and
    needle identification markers provided on two or more needles.

8. The specimen slicing apparatus according to claim 1, wherein the at least one link extends through an insertion hole formed in the base of each specimen slicing guide, such that the specimen slicing guides are slidable relative to each other along the at least one link.

9. The specimen slicing apparatus according to claim 1, wherein the needles of each specimen slicing guide extend in a straight row.

10. The specimen slicing apparatus according to claim 1, wherein the at least one link is at least substantially linear.

11. A specimen slicing kit for use in slicing a biopsy specimen taken from a human or an animal patient, comprising:
    a specimen slicing apparatus comprising:
        a first specimen slicing guide having a base extending in a longitudinal direction and a plurality of needles extending substantially perpendicularly from the base and being spaced along the longitudinal direction of the base, wherein distal ends of the needles are configured to pierce the biopsy specimen,
        a second specimen slicing guide having a base extending in a longitudinal direction and a plurality of needles extending substantially perpendicularly from the base and being spaced along the longitudinal direction of the base, wherein distal ends of the needles are configured to pierce the biopsy specimen and at least one link coupling the first and second specimen slicing guides in a spaced, parallel arrangement, wherein the first and second specimen slicing guides and the at least one link are configured to permit the spacing between the first and second specimen slicing guides to be adjusted while maintaining the needles of the first and second specimen slicing guides in a parallel relationship, and a support surface configured to support the biopsy specimen and to supportably receive the distal ends of the needles therein.

12. The specimen slicing kit according to claim 11, wherein the at least one link is at least substantially linear.

13. A specimen slicing apparatus comprising:

a first specimen slicing guide having a base extending in a longitudinal direction and a plurality of resiliently-elastic needles extending substantially perpendicularly from the base, wherein the needles are spaced along the longitudinal direction of the base and distal ends of the needles are configured to pierce the biopsy specimen, a second specimen slicing guide having a base extending in a longitudinal direction and a plurality of resiliently-elastic needles extending substantially perpendicularly from the base, wherein the needles are spaced along the longitudinal direction of the base and distal ends of the needles are configured to pierce the biopsy specimen, and at least one link extending through an insertion hole formed in the base of each specimen slicing guide, wherein the specimen slicing guides are slidable relative to each other along the at least one link while maintaining longitudinal axes of the needles of the first specimen slicing guide in a parallel relationship with longitudinal axes of the needles of the second specimen slicing guide and wherein the specimen slicing apparatus further comprises at least one visual reference selected from the group consisting of a plurality of gap identification markers provided on at least one of the bases, a plurality of needle identification markers provided on at least one of the bases, and needle identification markers provided on two or more needles of at least one of the bases.

14. The specimen slicing apparatus according to claim 13, wherein the at least one link is at least substantially linear.

15. A specimen slicing kit for use in slicing a biopsy specimen taken from a human or an animal patient, comprising:
the specimen slicing apparatus according to claim 1 and
a support surface configured to support the biopsy specimen and to supportably receive the distal ends of the needles therein.

16. A specimen slicing kit for use in slicing a biopsy specimen taken from a human or an animal patient, comprising:
the specimen slicing apparatus according to claim 4 and
a support surface configured to support the biopsy specimen and to supportably receive the distal ends of the needles therein.

17. A specimen slicing kit for use in slicing a biopsy specimen taken from a human or an animal patient, comprising:
the specimen slicing apparatus according to claim 6 and
a support surface configured to support the biopsy specimen and to supportably receive the distal ends of the needles therein.

18. The specimen slicing kit according to claim 17, wherein the at least one link is linear.

19. A method for slicing a biopsy specimen taken from a human or animal patient comprising:
(a) placing the biopsy specimen on a support surface,
(b) adjusting the spacing between the first and second specimen slicing guides of the specimen slicing apparatus of claim 1 to substantially correspond to the size of the biopsy specimen,
(c) fixing the biopsy specimen in position relative to the support surface by passing the distal ends of the needles of the first and second specimen slicing guides of the specimen slicing apparatus of claim 1 through the biopsy specimen and embedding the distal ends of the needles in the support surface,
(d) inserting a cutting tool through a corresponding pair of needle gaps in the two specimen slicing guides and
(e) downwardly moving the cutting tool through the biopsy specimen under the guidance of adjacent needles, thereby forming a tissue slice.

20. A method for slicing a biopsy specimen taken from a human or animal patient using the specimen slicing kit of claim 11 comprising:
(a) placing the biopsy specimen on the support surface of the specimen slicing kit of claim 11,
(b) adjusting the spacing between the first and second specimen slicing guides of the specimen slicing apparatus of claim 11 to substantially correspond to the size of the biopsy specimen,
(c) fixing the biopsy specimen in position relative to the support surface by passing the distal ends of the needles of the first and second specimen slicing guides of the specimen slicing apparatus of claim 11 through the biopsy specimen and embedding the distal ends of the needles in the support surface,
(d) inserting a cutting tool through a corresponding pair of needle gaps in the two specimen slicing guides and
(e) downwardly moving the cutting tool through the biopsy specimen under the guidance of adjacent needles, thereby forming a tissue slice.

* * * * *